United States Patent [19]

Sparks et al.

[11] 4,267,324

[45] May 12, 1981

[54] PROCESS FOR PREPARING 4-AMINOPYRAZOLO-(3,4-d)PYRIMIDINE

[75] Inventors: John W. Sparks, Boston; Henry Bader, Newton Center, both of Mass.

[73] Assignee: Polaroid Corporation, Cambridge, Mass.

[21] Appl. No.: 50,432

[22] Filed: Jun. 20, 1979

[51] Int. Cl.³ ............................................. C07D 487/04
[52] U.S. Cl. ...................................... 544/262; 548/377
[58] Field of Search .......................................... 544/262

[56] References Cited

U.S. PATENT DOCUMENTS

| | | | |
|---|---|---|---|
| 2,759,949 | 8/1956 | Hitchings et al. | 544/262 |
| 3,187,006 | 6/1965 | Druey et al. | 544/262 |
| 3,399,196 | 8/1967 | Druey et al. | 544/262 |
| 3,474,098 | 10/1969 | Hitchings et al. | 544/262 |
| 3,487,083 | 12/1969 | Cresswell et al. | 544/262 |
| 3,682,957 | 8/1972 | Cresswell et al. | 544/262 |
| 3,772,294 | 11/1973 | Podesva et al. | 544/262 |
| 3,948,913 | 4/1976 | Howarth et al. | 544/262 |

OTHER PUBLICATIONS

Robins, "J. Amer. Chem. Soc.", vol. 78, 1956, pp. 784–790.
Taylor et al., "J. Amer. Chem. Soc.", vol. 82, 1960, pp. 3138–3141.

*Primary Examiner*—Donald G. Daus
*Assistant Examiner*—James H. Turnipseed
*Attorney, Agent, or Firm*—Gaetano D. Maccarone

[57] ABSTRACT

There is described a process for synthesizing 4-aminopyrazolo(3,4-d)pyrimidine wherein 3-amino-4-cyanopyrazole is reacted with formamidine or a salt of formamidine at a temperature in the range of from about 85° C. to about 125° C.

7 Claims, No Drawings

PROCESS FOR PREPARING 4-AMINOPYRAZOLO-(3,4-d)PYRIMIDINE

BACKGROUND OF THE INVENTION

This application relates generally to a chemical process and, more particularly, to a process for synthesizing 4-aminopyrazolo(3,4-d)pyrimidine.

Processes for preparing 4-substituted pyrazolo(3,4-d)pyrimidines are known in the art. For example, U.S. Pat. No. 3,772,294 discloses a process for forming such compounds wherein a pyrimidine compound is reacted with hydrazine or hydrazine hydrate. An article by R. K. Robins in Jour. Amer. Chem. Soc. 78, 784–790 (1956), discloses a process wherein 3-amino-4-cyanopyrazole is reacted with formamide to give 4-aminopyrazolo(3,4-d)pyrimidine.

In the chemical synthesis art there is continuing interest in the discovery of new techniques for the synthesis of known materials. The present application is directed to a novel process for preparing 4-aminopyrazolo(3,4-d)pyrimidine.

SUMMARY OF THE INVENTION

It is therefore the object of this invention to provide a novel process for synthesizing 4-aminopyrazolo(3,4-d)pyrimidine.

It is another object to provide such a process wherein the reaction is carried out at a relatively low temperature.

It is a further object to provide such a process which gives a relatively high yield.

Another object is to provide such a process wherein the product is of high purity.

BRIEF SUMMARY OF THE INVENTION

These and other objects and advantages are accomplished in accordance with the invention by providing a process for synthesizing 4-aminopyrazolo(3,4-d)pyrimidine wherein 3-amino-4-cyanopyrazole is reacted with formamidine or a salt of formamidine at a relatively low temperature, that is, in the range of from about 85° to about 125° C. Generally, the 3-amino-4-cyanopyrazole and the formamidine or formamidine salt are combined in a solvent such as 2-methoxyethanol and heated to a temperature of from about 85° to about 125° C., preferably in an inert atmosphere, to give the desired 4-aminopyrazolo(3,4-d)pyrimidine. The final product is then recovered and, in a preferred embodiment, is purified to provide a highly pure material.

The formamidine and formamidine salts are more reactive than formamide within the process of the invention. In the experiment reported in the journal article of Robins referred to previously the reaction of 3-amino-4-cyanopyrazole with formamide was carried out at 193° C. Further, when in a manufacturing plant preparation the same process was carried out at 165° C. in an attempt to lower the reaction temperature, a period of about forty-eight hours was required to complete the conversion. The material obtained contained a significant amount of by-products of decomposition due to the lengthy thermal exposure and required extensive purification. The final product had a purity of about 85%.

Because of the higher reactivity of formamidine and formamidine salts the reaction of the present process can be carried out at the relatively low temperature specified above which results in less decomposition of the product and ultimately leads to higher yields of a very high purity product.

DESCRIPTION OF THE PREFERRED EMBODIMENTS

The process of the invention proceeds according to the following reaction:

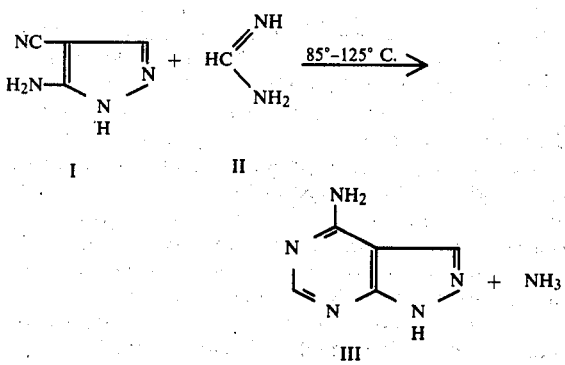

The reactants for the process of the invention are commercially available and can also be prepared by reactions which are known to those skilled in the art. According to one reaction sequence, 3-amino-4-cyanopyrazole may be prepared by initially reacting triethyl orthoformate and malononitrile in acetic anhydride to form ethoxymethylenemalononitrile and then reacting the latter with hydrazine hydrate. Ethoxymethylenemalononitrile and its solutions are toxic and can cause severe allergenic reactions from both skin contact and vapor inhalation. According to a preferred embodiment of the process of the invention the ethoxymethylenemalononitrile is produced in-situ and, without being isolated, is reacted with hydrazine hydrate to give the desired 3-amino-4-cyanopyrazole. In this manner the difficulties attendant to the handling of ethoxymethylenemalononitrile are greatly reduced.

In the formation of ethoxymethylenemalononitrile by the reaction described above ethyl acetate and acetic acid are produced as by-products. These by-products may be removed from the reaction mixture by either of two techniques. According to the preferred embodiment the ethyl acetate and acetic acid are removed from the reaction mixture by distillation. In this process some ethoxymethylenemalononitrile codistills to the extent that it may constitute up to about 1% of the distillate. Hence, the receiving vessel should contain a sufficient amount of a dilute aqueous amine such as ammonia, diethylamine or hydrazine for the hydrolysis of the ethoxymethylenemalononitrile which proceeds readily at about 25° C. Careful dilution of the residue of molten ethoxymethylenemalononitrile with a solvent such as isopropanol or methanol followed by cooling, slow addition of hydrazine hydrate at about 20° C. and holding at about 35° C. allows for a high degree of conversion to 3-amino-4-cyanopyrazole. The solvent may then be removed by distillation, replaced by water and the aqueous solution clarified such as by treatment with charcoal before the desired product crystallizes.

In another embodiment refluxing is substituted for distillation during the synthesis thereby retaining the ethyl acetate and acetic acid in the reaction mixture. Subsequently the hydrazine hydrate can be added slowly at about 20° C. and a high degree of conversion to the desired product can be achieved in the presence of the acetic acid. To isolate the product the acetic acid can be neutralized by adding dilute sodium hydroxide and azeotropic distillation of ethyl acetate will complete the removal of the by-products. Crystallization gives a crude 3-amino-4-cyanopyrazole that is then preferably recrystallized, with charcoal treatment, from water.

Conversion of the 3-amino-4-cyanopyrazole to 4-aminopyrazolo(3,4-d)pyrimidine is then achieved by reacting the former with formamidine or a salt of formamidine in a solvent such as 2-methoxyethanol at a temperature of from about 85° C. to about 125° C. for a period of from about one to about seventy-two hours. Since free formamidine base has limited stability under ambient conditions, it is preferred to employ a salt of formamidine in the process of the invention. Any suitable formamidine salt such as the acetate or hydrochloride salts may be employed. Where salts of strong acids such as the hydrochloride salt are used it is necessary to liberate formamidine by addition of a suitably strong base to the reaction mixture such as, for example, sodium acetate, sodium methoxide and the like.

The reaction is preferably carried out at a temperature of about 100° C. for a period of about 48 hours. Higher temperatures for shorter periods of time tend to produce colored impurities. Any suitable solvent may be used such as, for example, 2-methoxyethanol, 2-ethoxyethanol, n-propanol and the like. The assay of the crude final product is typically uniformly high and under optimum conditions typically exceeds 97%. The quality of the crude 4-aminopyrazolo(3,4-d)pyrimidine is strongly dependent upon the quality of the 3-amino-4-cyanopyrazole used in the synthesis and since the former is more difficult to purify, particularly insofar as removing colored impurities, control of the purity of the latter is very important to the process.

The crude 4-aminopyrazolo(3,4-d)pyrimidine is then collected from the reaction mixture such as by filtration and preferably purified such as by washing with a solvent.

The pure product made according to the preferred embodiment of the invention is suitable for use in dye developer photographic diffusion transfer applications as are disclosed in U.S. Pat. No. 3,899,331.

The invention will now be described further in detail with respect to specific preferred embodiments by way of examples, it being understood that these are intended to be illustrative only and the invention is not intended to be limited to the materials, conditions, process parameters, etc., which are recited therein. All parts and percentages are by weight unless otherwise recited.

EXAMPLE I

Preparation of 3-Amino-4-cyanopyrazole

Exactly 132 g (2.0 m) of malononitrile and 440 g (4.32 m) of acetic anhydride were mixed and heated under nitrogen to about 110° C. for a period of about 45 minutes. Triethyl orthoformate (304 g, 2.1 m) was added to the mixture over a 40-minute period with distillation commencing as the addition ended. It should be noted that the exothermic reaction can be controlled by the rate of addition to keep the temperature at about 108°-112° C. The receiving vessel for the distillate was equipped with a stirrer and contained a solution of 68 ml of ammonium hydroxide (1.0 m $NH_3$) and 132 ml of water. Distillation was carried for about 1½ hours at atmospheric pressure until the vessel temperature exceeded 115° C. Vacuum was then gradually applied (>100 mm) and the distillation continued for about 1 hour until the vessel temperature reached 125° C. During the initial stages of the distillation the walls of the receiving vessel were coated with ammonium salts and the liquid contained two phases. As the relative amount of acetic acid increased in the distillate the ammonium salts dissolved and in the last stages of the distillation the liquid became homogeneous.

The molten ethoxymethylenemalononitrile was allowed to cool to about 65° C. and then isopropanol (400 ml) was added over a 30-minute period, the temperature over the first half of the addition being held at about 65° C. to prevent crystallization. The temperature of the mixture should not exceed 65° C. since an exothermic reaction between isopropanol and ethoxymethylenemalononitrile can occur which could result in poor quality of the desired 3-amino-4-cyanopyrazole. The solution was cooled to 10° C. and hydrazine hydrate (112 g, 2.24 m) was added dropwise over a 2½ hour period with cooling. The resulting slurry was then heated to about 20° C. for about 1 hour followed by heating for about 1 hour at about 35° C. The mixture was then heated to 65° C. and 50 ml of water added. The isopropanol was removed by distillation under a slight vacuum at a temperature of about 60°-63° C. over a 2½ hour period with an additional 350 ml of water being added in 50 ml portions every 20 minutes. A total of 440 ml of distillate was collected.

The dark red colored solution was cooled over a 2-hour period to 0°-5° C. and held at that temperature for about 1 hour. A light tan solid was collected by filtration and rinsed with 150 ml of 5° C. water. After reslurrying the solid in 400 ml of water at 0°-5° C. the solid was again filtered and rinsed with 150 ml of water. The product, after drying at 65° C.-75° C. under vacuum for 18 hours, weighed 134.5 g (62% yield) and had a melting point of 172°-174° C.

Preparation of 4-Aminopyrazolo(3,4-d)pyrimidine

Exactly 10.0 g (0.093 m) of 3-amino-4-cyanopyrazole, 2.0 of charcoal and 1.0 of diatomaceous earth were stirred in 100 ml of 2-methoxyethanol at about 25° C. for about 2 hours and filtered under nitrogen into a reaction flask. Formamidine acetate (11.5 g; 0.11 m; m.p. 163°-164° C.) was added to the flask and the resulting amber-colored mixture heated under nitrogen at about 100° C. for about 48 hours. A clear solution was obtained above 60° C. and crystals began appearing at about 95° C. The mixture was cooled to about 20° C. and a light tan solid was collected by filtration and washed with two 25 ml portions of methanol. The solid was dried at about 70° C. under vacuum to give 9.46 g (76% yield) which was assayed at 99% purity by liquid chromatography.

The dried 4-aminopyrazolo(3,4-d)pyrimidine was further purified by initially suspending 3.5 g in 25 ml of toluene at about 25° C. and acetic acid (25 ml) was added to the suspension with rapid stirring over a 1 hour period. The slurry thickened during the course of the addition; however, after stirring for about 18 hours at about 25° C. the mixture thinned. The fine crystalline product was filtered and rinsed with 10 ml of 1:1 toluene/acetic acid (V/V) and then with 10 ml of toluene. The product was dried at about 90° C. for about 2 hours under vacuum to give 3.23 g (92% yield) of a white powder which was assayed at 99.9% purity by liquid chromatography: IR(NUJOL) was identical to that of a known sample; 3315(m), 1675(s), 1590(s) and 962 cm$^{-1}$(s).

EXAMPLE II

Exactly 66 g (1.0 m) of malononitrile, 152 g (1.03 m) of triethyl orthoformate and 220 g (2.15 m) of acetic anhydride were mixed and carefully heated to about 115° C. The reaction is exothermic above 110° C. and needed intermittent cooling and heating to maintain the desired temperature. After the reaction mixture was held at about 115° C. for about 20 minutes distillation of the accumulating ethyl acetate and acetic acid began (b.p. 77°–91° C.). Distillation was continued by holding the reaction temperature at about 115° C. for about 40 minutes. The receiving flask for the distillate contained dilute aqueous ammonia to neutralize any ethoxymethylenemalononitrile which codistilled. Vacuum was then applied (>100 mm) and the remainder of the residual by-products collected (b.p. 75°–85° C.) over a period of about 40 minutes. The total volume of distillate collected was 290 ml (excluding the aqueous volume). Full atmospheric pressure was restored with nitrogen, the temerature of the molten ethoxymethylenemalononitrile lowered to about 60° C. and 200 ml of methanol carefully added over a 10-minute period. The solution was cooled to about 20° C. and 56 g (1.12 m) hydrazine hydrate added dropwise over 30 minutes while maintaining the temperature between about 18° and 22° C. After holding at about 20° C. for about 30 minutes the reaction mixture was allowed to warm to about 35° C. and held there for about 1 hour. A delayed exothermic reaction occurs at this state and careful temperature control is required.

The methanol was removed by heating the mixture until about half the methanol was distilled and then adding 200 ml of water to force nearly complete removal. In all about 210 ml (b.p. 60°–75° C.) was collected. A slight vacuum was applied toward the end of the distillation so that the temperature of the vessel was kept below 85° C. The vessel temperature was lowered to about 75° C. and about 12 g of charcoal added after stirring for about 10 minutes to about 85° C. the mixture was filtered through diatomaceous earth and the amber-colored filtrate then cooled. The mixture was stirred at 0°–5° C. for about 1 hour and then filtered and the filtrate washed with cold water. The yield of the light tan solid 3-amino-4-cyanopyrazole (m.p. 175°–176° L C.) was 59.6 g (55% yield).

EXAMPLE III

Exactly 16.5 g (0.25 m) of malononitrile, 38 g (0.26 m) of triethyl orthoformate and 55 g (0.54 m) of acetic anhydride were mixed and carefully heated to about 115° C. After the reaction mixture was held at about 115° C. for about 20 minutes, vigorous reflux ensued indicating the accumulation of the ethyl acetage and acetic acid by-products. Reflux was continued for about 2 hours during which time the reflux temperature dropped to about 98° C. The mixture was cooled to about 20° C. and hydrazine hydrate (15.5 g, 0.31 m) was added dropwise over a 40 minute period while maintaining the temperature between 18° and 22° C. After holding at 20°–30° C. for about 18 hours, the mixture, a solid-liquid slurry, was neutralized at about 25° C. to pH 7 with a solution of 36 g of 50% sodium hydroxide in 72 ml of water. The mixture was then heated and the ethyl acetate removed by azeotropic distillation (b.p. 68°–71° C.), the total volume of distillate collected being 45 ml. The solution was cooled and held at 0°–5° C. for about 1½ hours. The light tan solid was collected and rinsed with cold water to give 19.2 g (71% yield) m.p. 170° C.

A total of 10 g of the crude product was heated with 2.0 g of charcoal and 1.0 g of diatomaceous earth in 50 ml. of water. The mixture was held at 85°–95° C. for about 10 minutes before filtration. The mixture was filtered at about 80° C. and the filtrate cooled to 0°–5° C. and held at that temperature for about 2 hours. The 3-amino-4-cyanopyrazole was collected by filtration to give 7.5 g (75% yield, 53% overall yield) m.p. 176° C.

EXAMPLE IV

Exactly 10.0 g. (0.093 m) of 3-amino-4-cyanopyrazole, 2.0 g of charcoal and 1.0 g of diatomaceous earth were stirred in 75 ml of 2-methoxyethanol at about 25° C. for about 2 hours. The mixture was filtered under nitrogen into a reaction flask. Formamidine acetate (11.5 g; 0.11 m) m.p. 163°–164° C. and an additional 25 ml of 2-methoxyethanol were added and the mixture heated under nitrogen at about 100° C. for about 48 hours. The mixture was cooled to about 20° C. and the white solid collected by filtration and washed with two 25 ml portions of methanol. The 4-aminopyrazole(3,4-d)pyrimidine was dried to give 9.70 g (78% yield) which was assayed at 97.5% purity by liquid chromatography: IR(NUJOL) was identical to that described in Example I.

EXAMPLES V–IX

These examples illustrate the effect of reaction time and temperature on the yield of 4-aminopyrazolo(3,4-d)pyrimidine. The reactions were carried out with 3-amino-4-cyanopyrazole from the same lot (m.p. 175°–176° C.) and formamidine acetate from the same lot. The reactions were carried out as described in Example I using the same relative amounts of the reactants with the exception that the 3-amino-4-cyanopyrazole was not pretreated with charcoal and diatomaceous earth. The results are shown in Table I.

TABLE I

| Example | Time (hrs) | Temp (°C.) | Yield (%) |
| --- | --- | --- | --- |
| V | 1 | 125 | 66 |
| VI | 3 | 125 | 69 |
| VII | 1 | 100 | 26 |
| VIII | 3 | 100 | 45 |
| IX | 48 | 100 | 74 |

Although the invention has been described in detail with respect to various preferred embodiments thereof, these are intended to be illustrative only and not limiting of the invention but rather those skilled in the art will recognize that modifications and variations may be made therein which are within the spirit of the invention and the scope of the appended claims.

What is claimed is:

1. A process for synthesizing 4-aminopyrazolo (3,4-d)pyrimidine which comprises the step of reacting 3-amino-4-cyanopyrazole with formamidine or a salt of formamidine in the presence of a solvent at a temperature in the range of from about 85° C. to about 125° C.

2. The process as defined in claim 1 wherein formamidine acetate is reacted with 3-amino-4-cyanopyrazole.

3. The process as defined in claim 1 wherein the reaction is carried out for a period of about one to about seventy-two hours.

4. The process as defined in claim 1 wherein the reaction is carried out at a temperature of about 100° C. for about forty-eight hours.

5. The process as defined in claim 1 wherein said 3-amino-4-cyanopyrazole is formed by steps comprising initially reacting triethyl orthoformate and malononitrile in acetic anhydride to form ethoxymethylenemalononitrile and without isolating said ethoxymethylenemalononitrile, reacting said ethoxymethylenemalononitrile with hydrazine hydrate to form said 3-amino-4-cyanopyrazole.

6. The process as defined in claim 1 wherein the reaction is carried out in an inert atmosphere.

7. The process as defined in claim 1 and further including the step of purifying said 4-aminopyrazolo(3,4-d)pyrimidine.

* * * * *